(12) United States Patent
Vilsmeier et al.

(10) Patent No.: US 6,428,547 B1
(45) Date of Patent: Aug. 6, 2002

(54) DETECTION OF THE SHAPE OF TREATMENT DEVICES

(75) Inventors: Stefan Vilsmeier, Kufstein (AT); Rainer Birkenbach, Feldkirchen (DE)

(73) Assignee: BrainLAB AG, Heimstetten (DE)

( * ) Notice: Subject to any disclaimer, the term of this patent is extended or adjusted under 35 U.S.C. 154(b) by 0 days.

(21) Appl. No.: 09/713,358

(22) Filed: Nov. 15, 2000

(30) Foreign Application Priority Data

Nov. 25, 1999 (DE) .......................................... 199 56 814

(51) Int. Cl.[7] .............................................. A61B 19/00
(52) U.S. Cl. ...................................... 606/130; 600/424
(58) Field of Search .......................... 606/130; 600/424, 600/426

(56) References Cited

U.S. PATENT DOCUMENTS

| | | | | |
|---|---|---|---|---|
| 5,300,080 A | * | 4/1994 | Clayman | 606/130 |
| 5,769,861 A | * | 6/1998 | Vilsmeier | 606/130 |
| 5,797,849 A | * | 8/1998 | Vesely et al. | 600/461 |
| 5,868,673 A | * | 2/1999 | Vesely | 600/407 |
| 5,891,158 A | * | 4/1999 | Manwaring et al. | 606/130 |
| 6,048,312 A | * | 4/2000 | Ishrak et al. | 600/443 |
| 6,076,008 A | * | 6/2000 | Bucholz | 600/427 |
| 6,112,113 A | * | 8/2000 | Van Der Brug et al. | 600/427 |
| 6,149,592 A | * | 11/2000 | Yanof et al. | 600/427 |
| 6,175,756 B1 | * | 1/2001 | Ferre et al. | 600/424 |
| 6,195,577 B1 | * | 2/2001 | Truwit et al. | 600/411 |
| 6,214,019 B1 | * | 4/2001 | Manwaring et al. | 606/130 |
| 6,246,898 B1 | * | 6/2001 | Vesely et al. | 600/424 |
| 6,275,725 B1 | * | 8/2001 | Cosman | 600/426 |
| 6,298,262 B1 | * | 10/2001 | Franck et al. | 600/426 |

FOREIGN PATENT DOCUMENTS

| | | |
|---|---|---|
| WO | 99/58055 | 11/1999 |
| WO | 99/58065 | 11/1999 |

* cited by examiner

*Primary Examiner*—Jeffrey A. Smith
*Assistant Examiner*—Michael B. Priddy
(74) *Attorney, Agent, or Firm*—Renner, Otto, Boisselle & Sklar, LLP

(57) ABSTRACT

The invention relates to a method of detecting the shape of a treatment device (3), in which the treatment device (3) is referenced in a computer-controlled, camera-assisted navigation system by means of a positional marker array (4) attached to the treatment device (3), wherein, by means of at least one radiographic image, projections of the treatment device (3) are detected and, via the position of the positional marker array (4) in the projections, the total outer shape of the treatment device (3) is assigned in the navigation system.

8 Claims, 1 Drawing Sheet

DETECTION OF THE SHAPE OF TREATMENT DEVICES

BACKGROUND OF THE INVENTION

1. Technical Field

The present invention relates to a method of detecting the shape of a treatment device, in which the treatment device is referenced in a computer-controlled, camera-assisted navigation system by means of a positional marker array attached to the treatment device.

2. Description of Related Art

Known from German patent specification DE 196 39 615 is a navigation system for the camera-assisted tracking of surgical instruments during an operation. For this purpose, reflectors are applied to the instruments which are recognized via a camera system and a connected computer unit and localized three-dimensionally. It is herein proposed to pre-reference each instrument separately in the navigation system so that the position of its tip is known to thus enable the surgeon to establish from the monitor display where the tip of the instrument is located in each case relative to the previously referenced body parts of the patient. One disadvantage of such a navigation system becomes apparent as soon as e.g. instruments are used which do not form a straight line from handle to tip, as is the case, for example, with an awl having a curved front section.

A navigation system of the aforementioned kind, can merely indicate the position of the tip of such an awl, but is unable to display to the surgeon where the curved section of the instrument is at any one time. This is particularly critical when sensitive tissue regions are being operated on, for instance in the brain, since curved sections of an instrument, the position of which cannot be seen, may cause damage upon movement.

The same applies to navigating larger or bulky treatment devices such as, for example, saws for bone surgery, drills, screws or all possible implants.

SUMMARY OF THE INVENTION

It is thus an objective of the present invention to provide a method which enables the referencing of treatment devices of any outer shape within a navigation system such that information about the outer shape of the treatment device is made available during treatment.

This objective is met in accordance with the invention by a method of detecting the shape of a treatment device, in which the treatment device is referenced in a computer-controlled, camera-assisted navigation system by means of a positional marker array attached to the treatment device, wherein, by means of at least one radiographic image, projections of the treatment device are detected and, via the position of the positional marker array in the projections, the total outer shape of the treatment device is assigned in the navigation system.

By means of the method in accordance with the invention, the outer shape of a treatment device is entirely known in the navigation system, and this information is available to the acting surgeon during treatment. Advantageously, the acting surgeon is now able with the aid of the navigation system to avoid certain parts of the treatment device damaging the patient tissue since information as to the position of the outer contours of the treatment device is made available to him at all times by image-assisted navigation. Thus, operations can now be performed using, for example, treatment devices such as an awl without causing injury to the patient; this applying, among other things, to inserting implants.

Preferably, computer-controlled assignment of the outer shape with the method in accordance with the invention is achieved by processing the projection image data and the data of the navigation system in a single computer unit with a single monitor display.

Thus, the apparatus needed is reduced and the surgeon can access all the required information from a single source.

At least two radiographic images of the treatment device can be made in different positions to detect their outer shape three-dimensionally. As an alternative, it is possible to make a more lengthy radiographic image, during which the treatment device is moved, the assignment being done from the projections of the treatment devices and the positional marker array in the movement sequence or at individual points in time during the movement sequence.

If necessary, assignment of the outer shape may be done several times in sequence during treatment, to be on the safe side.

In accordance with a preferred embodiment of the method in accordance with the invention, a system including reflector arrays applied to all devices used in treatment for the radiation of a source of invisible light, in particular a source of infrared radiation, is used as the camera-assisted navigation system.

It is particularly of advantage to use a C-bow x-ray unit, in particular a fluoroscope device, to produce the radiographic image. Such a C-bow x-ray unit or fluoroscope device may be applied to the patient directly before or during the operation so that the necessary radiographic images can be produced in situ.

In accordance with a further aspect of the invention, it relates to a method of referencing treatment devices, in which the shape of several treatment devices is detected by a method as described above. In other words, also several treatment devices, which are required for instance during an operation (for example, surgical implements and implants) may be detected by their outer shape in accordance with the invention.

BRIEF DESCRIPTION OF THE DRAWINGS

The invention will now be further detailed by way of an embodiment. In the attached drawings.

DETAILED DESCRIPTION OF THE PREFERRED EMBODIMENTS

Figure 1:
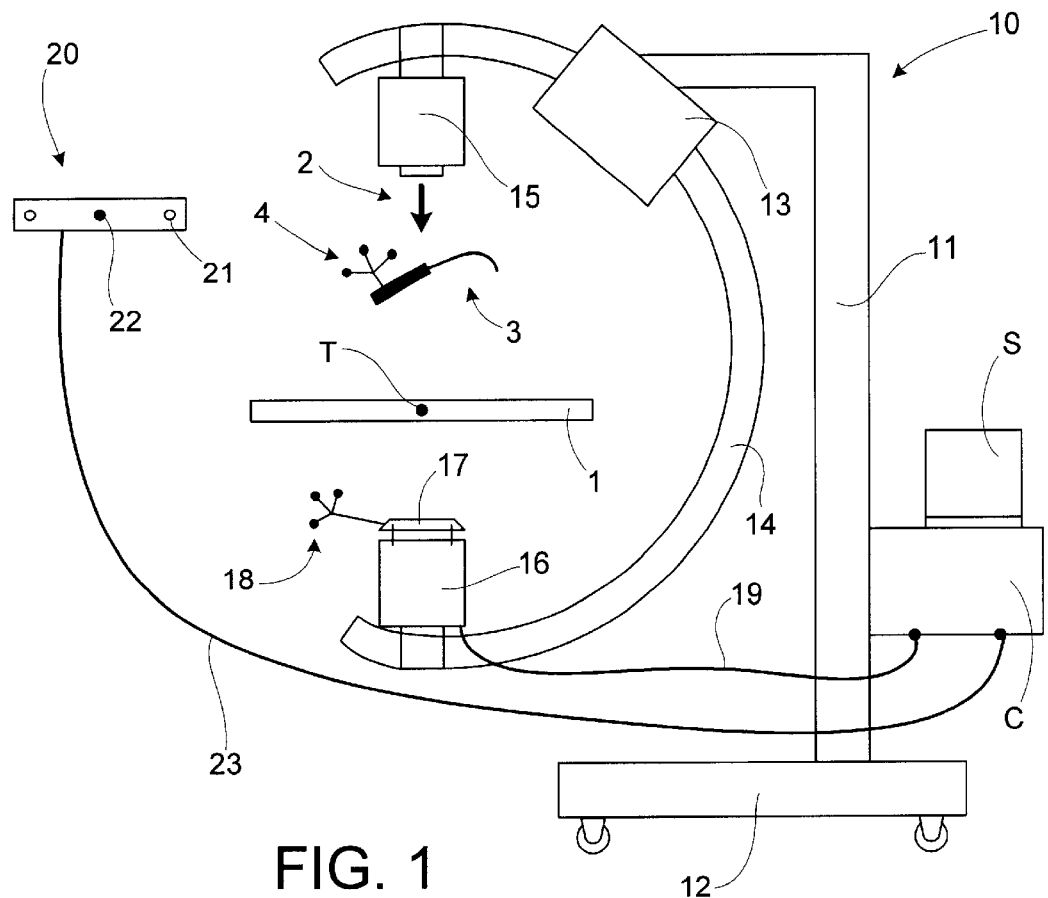
FIG. 1 is a principal representation of an x-ray unit which is combined with a camera-assisted navigation system; an awl (as an example of a surgical instrument (treatment device)) is brought into the detection range of the x-ray unit.

FIG. 1 illustrates a single-line drawing of an x-ray unit, including a camera-assisted navigation system. To be operated on is a target of treatment T in the body 1 of the patient, indicated schematically. For this purpose, a C-bow x-ray unit 10 is used, which stands on a base 12 which may be rolled and locked in position. Attached to the arm 11 is the guide 13 for the bow 14, shiftably and fixedly mounted thereon. The bow has at its upper part an x-ray source 15 and, diametrically opposed thereto, an image amplifier 16, the image signals of which are communicated by means of a cable 19 to the computer (C) with display S, which is likewise secured to the arm.

A reference structure 17 is arranged on the image amplifier 16 via a mount, which is merely indicated by dashes, not shown in FIG. 1. The computer C receives additional positional data from the camera unit 20 via the cable 23. The camera unit 20 comprises two infrared cameras 21 and a source of infrared radiation 22. It can be directly secured to the C-bow x-ray unit 10. By means of this camera unit, the position of the positional marker arrays is determined, for example, a positional marker array 18 at the reference structure 17 or a positional marker array 4 at an awl 3, and thus the position of these instruments themselves.

To detect the outer shape of a treatment device, in the present example the awl 3, by the method in accordance with the invention, the awl 3 is located between the radiation source 15 and the image amplifier 16 of the x-ray unit as shown in FIG. 1 schematically. Applied to the awl 3, for example via an adapter, is a positional marker array 4, by means of which the position of the awl 3 can be referenced in the camera-assisted navigation system. Then, with the aid of the method in accordance with the invention, the respective outer shape of the awl 3 in each position can be additionally referenced so that not only—as usual hitherto—the position of the tip of the awl 3 is displayed on the monitor S, but also its complete shape.

In the present example embodiment this is done as follows: The awl 3 is first referenced as usual in the camera-assisted navigation system, i.e. by means of the positional marker array 4, which reflects the radiation of the source of infrared radiation 22, recognized and assigned by the infrared cameras 21. Subsequently, the awl 3 is brought into the detection range of the C-bow x-ray unit 10, i.e. between the x-ray source 15 and image amplifier 16.

Figures 2A, 2B, 2C:
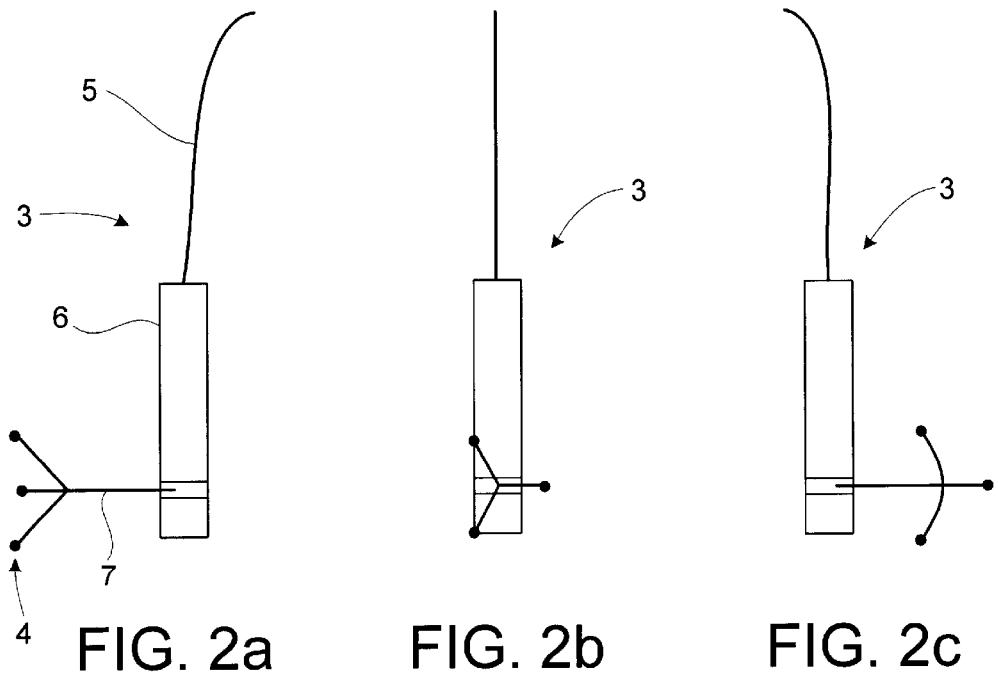
FIGS. 2a, 2b and 2c schematically show such an awl in various positions, for which a radiographic image is produced to detect the shape three-dimensionally.

After this, three radiographic images are then produced in the present example embodiment, the awl 3 being placed in another position after each radiographic image produced, for example, by the surgeon holding the awl 3 by the handle 6 and turning it at a specific angle each time. The projections of the awl 3, as they appear for instance in the produced radiographic images, are shown in FIGS. 2a to 2c. here, the awl 3 is still somewhat magnified schematically, and comprises the handle 6 as well as a front section 5, which is curved towards the tip. Arranged at the handle 6 via an adapter 7 is a positional marker array 4 including three positional markers.

The three images (projections) of the awl 3 shown in FIGS. 2a to 2c are made in sequence. The surgeon thus firstly holds the awl so that it assumes a position shown in FIG. 2a. In this position, a radiographic image is made, in which, on the one hand, the positional marker array 4 is detected and, on the other, information as to the outer shape of the awl 3 in this position is also detected. Due to the array of the positional markers, the position of the awl 3 is recognized three-dimensionally via the navigation system.

Thus, the outer shape of the awl 3, as represented in this position, can be computer-assistedly assigned by processing the radiographic image.

To then detect the shape of the awl 3 three-dimensionally and to also assign this data three-dimensionally, the awl 3 is turned by the surgeon, i.e. into a position as shown for example in FIG. 2b. It is evident that both the shape of the awl 3 in this projection as well as the array of the positional markers changes, and by linking this data a three-dimensional shape of the awl 3 can already be assigned in the navigation system with good accuracy. To further enhance the accuracy, another radiographic image (or as often as is needed) is made of another turned position, as shown in FIG. 2c, after which, via position and shape computations, the outer shape of the awl 3 is made available as data in the navigation system. The linkage point between the shape and position detection data is always the positional marker array 4, which is detectable by both the navigation system and in the radiographic images.

With the aid of this information about the outer shape of the awl 3, the surgeon is now able to recognize from the display S of the navigation system not only the tip, but also the entire awl 3, and thus exclude any risk of injury, which exists when, in particular, the position of the curved front section 5 is not precisely known during the operation.

Although not represented in the figures, any treatment device whatsoever can be assigned in its shape in the navigation system, i.e. saws for bone surgery, implants, drills, screws, etc. Furthermore, instead of the three radiographic images, a more lengthy radiographic image may be made, during which the treatment device is moved, wherein the assignment is done from the projections of the treatment devices and the positional marker array in the movement sequence or at the individual points in time during the movement sequence.

In the foregoing description, preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A method of detecting the shape of a treatment device, wherein said treatment device is referenced in a computer-controlled, camera-assisted navigation system by means of a positional marker array attached to said treatment device, wherein projections of said treatment device are detected by means of at least one radiographic image, and the total outer shape of said treatment device is assigned in the navigation system via the position of said positional marker array in said projections.

2. The method as set forth in claim 1, wherein assigning said outer shape is achieved by processing radiographic image data and data from said navigation system in a single computer (C) with a single monitor display (S).

3. The method as set forth in claim 1, wherein at least two radiographic images of said treatment device are made in different positions.

4. The method as set forth in claim 1, wherein a radiographic image is made during which said treatment device is moved to create a radiographic image having a movement sequence showing the positional marker array at a series of individual points in time, said assignment being done from said projections of said treatment device and said positional marker array in the movement sequence or at individual points in time during said movement sequence.

5. The method as set forth in claim 1, wherein the assignment of said outer shape is done several times in sequence during treatment.

6. The method as set forth in claim 1, wherein a system including reflector arrays applied to all devices used in treatment for the radiation of a source of invisible light, in particular a source of infrared radiation, is used as said camera-assisted navigation system.

7. The method as set forth in claim 1, wherein a C-bow x-ray unit, in particular a fluoroscope device, is used for producing said radiographic image.

8. A method of referencing treatment devices, in which the shape of several treatment devices is detected by a method as set forth in claim 1.

* * * * *